(12) United States Patent
DeMarco

(10) Patent No.: US 7,404,893 B2
(45) Date of Patent: *Jul. 29, 2008

(54) CHROMATOGRAPHY CARTRIDGE AND METHOD FOR MANUFACTURING A CHROMATOGRAPHY CARTRIDGE

(75) Inventor: Nicholas DeMarco, Burlington, WI (US)

(73) Assignee: Varian, Inc., Palo Alto, CA (US)

( * ) Notice: Subject to any disclaimer, the term of this patent is extended or adjusted under 35 U.S.C. 154(b) by 344 days.

This patent is subject to a terminal disclaimer.

(21) Appl. No.: 11/054,846

(22) Filed: Feb. 9, 2005

(65) Prior Publication Data

US 2005/0133426 A1  Jun. 23, 2005

Related U.S. Application Data

(63) Continuation-in-part of application No. 10/775,451, filed on Feb. 10, 2004, now Pat. No. 7,351,332.

(60) Provisional application No. 60/512,129, filed on Oct. 17, 2003.

(51) Int. Cl.
   *B01D 15/08* (2006.01)
(52) U.S. Cl. .................... 210/198.2; 210/656
(58) Field of Classification Search .......... 210/198.2, 210/635, 656, 232, 282; 95/82; 96/101, 96/103, 106; 156/73.5; 264/248
   See application file for complete search history.

(56) References Cited

U.S. PATENT DOCUMENTS

| 4,831,244 | A | * | 5/1989 | Slafer et al. | 235/487 |
|---|---|---|---|---|---|
| 4,959,406 | A | * | 9/1990 | Foltin et al. | 524/413 |
| 5,601,708 | A | | 2/1997 | Leavesley | |
| 5,693,223 | A | * | 12/1997 | Yamada et al. | 210/198.2 |
| 6,001,253 | A | | 12/1999 | Conroy et al. | |
| 6,068,766 | A | | 5/2000 | Van Davelaar | |
| 6,074,556 | A | | 6/2000 | Van Davelaar | |
| 6,090,278 | A | | 7/2000 | Lally et al. | |
| 6,117,329 | A | | 9/2000 | Hargro | |
| 6,132,605 | A | | 10/2000 | Leavesley et al. | |
| 6,139,733 | A | | 10/2000 | Hargro et al. | |
| 6,171,486 | B1 | | 1/2001 | Green et al. | |
| 6,221,252 | B1 | | 4/2001 | Hargro et al. | |
| 6,294,087 | B1 | | 9/2001 | Hargro et al. | |
| 6,398,953 | B1 | | 6/2002 | Hargro | |
| 6,436,284 | B1 | | 8/2002 | Leavesley et al. | |
| 6,565,745 | B2 | | 5/2003 | Hodgin et al. | |
| 6,730,216 | B2 | * | 5/2004 | Heringa et al. | 210/198.2 |
| 6,776,933 | B1 | * | 8/2004 | Chatwin et al. | 264/1.34 |

(Continued)

OTHER PUBLICATIONS

ISCO product brochure #2291: "CombiFlash™ Organic Purification Systems for Isco;" Oct. 1999; 4 pages; Statement of Relevance attached.

(Continued)

*Primary Examiner*—Ernest G Therkorn

(57) ABSTRACT

A chromatography cartridge. In some embodiments, the chromatography cartridge can include a tubular housing defining a longitudinal axis and including a relatively non-laser-writable first portion, and a relatively laser-writable second portion. The relatively laser-writable second portion can be positioned substantially parallel to the longitudinal axis and can define at least a portion of an outer surface of the tubular housing to allow data to be printed on the outer surface of the tubular housing with a laser.

26 Claims, 6 Drawing Sheets

U.S. PATENT DOCUMENTS

| | | |
|---|---|---|
| 6,949,194 B2 | 9/2005 | Hodgin et al. |
| 7,125,489 B2 * | 10/2006 | Zelechonok et al. ..... 210/198.2 |
| 7,351,332 B2 * | 4/2008 | DeMarco ................. 210/198.2 |
| 2002/0077380 A1 * | 6/2002 | Wessels et al. ................. 522/2 |
| 2002/0167692 A1 * | 11/2002 | Cunningham .................. 359/2 |
| 2004/0084375 A1 | 5/2004 | Hodgin et al. |
| 2005/0199540 A1 * | 9/2005 | Zelechonok et al. ..... 210/198.2 |
| 2005/0242018 A1 | 11/2005 | Hodgin et al. |
| 2007/0026184 A1 * | 2/2007 | Ehreiser et al. ............... 428/43 |

OTHER PUBLICATIONS

Sample of Biotage Si 25+M 0085-2 chromatography cartridge with printing, available at least as early as Feb. 9, 2004.

* cited by examiner

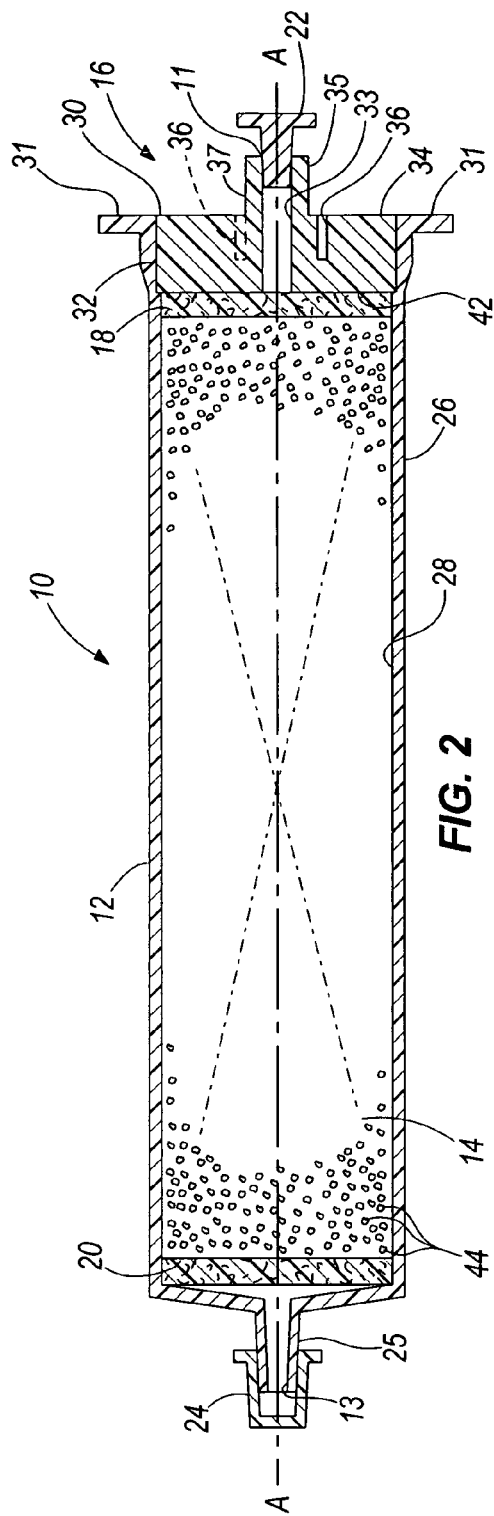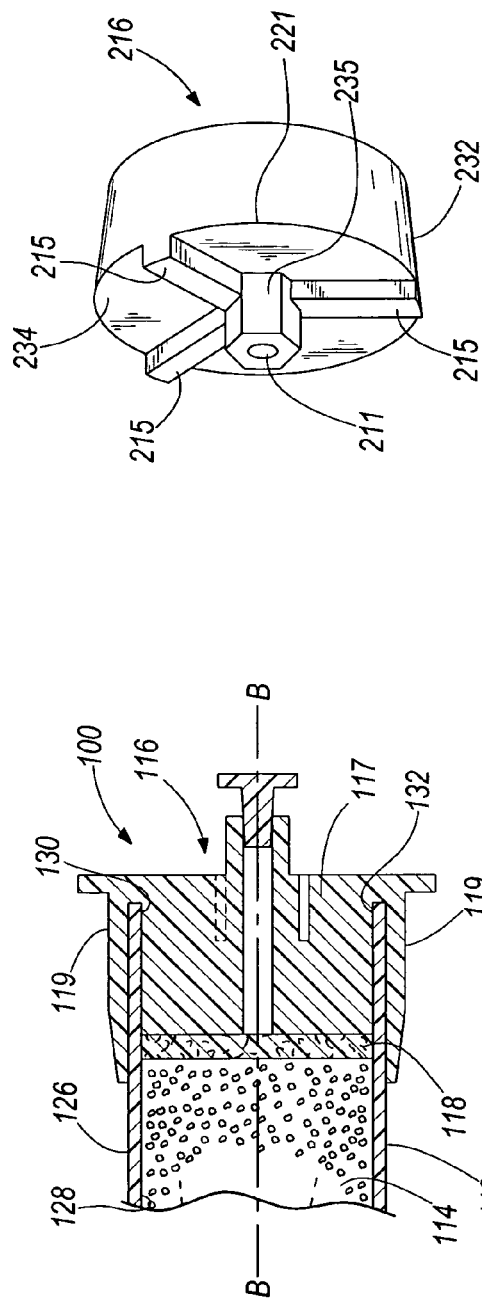

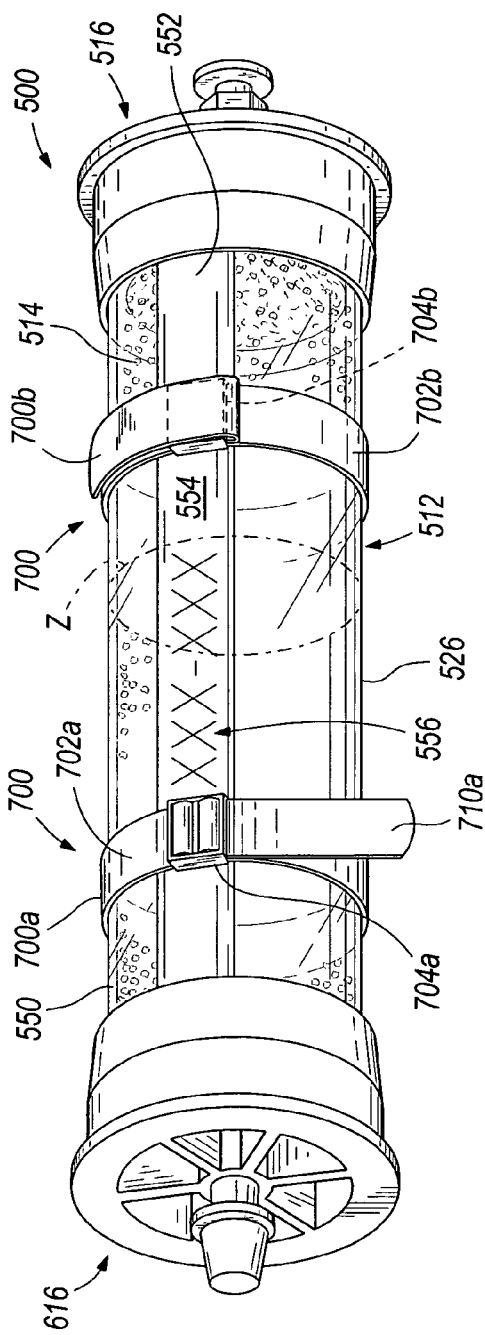
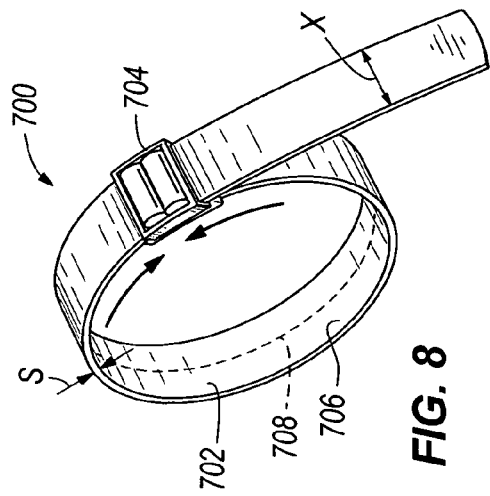
FIG. 8
FIG. 9

CHROMATOGRAPHY CARTRIDGE AND METHOD FOR MANUFACTURING A CHROMATOGRAPHY CARTRIDGE

RELATED APPLICATIONS

This is a continuation-in-part of U.S. patent application Ser. No. 10/775,451 filed Feb. 10, 2004 now U.S. Pat. No. 7,351,332, which is incorporated herein by reference, and which claims the benefit of U.S. Provisional Patent Application Ser. No. 60/512,129, filed Oct. 17, 2003, which is incorporated herein by reference.

BACKGROUND OF THE INVENTION

Chromatography columns or cartridges typically contain a densely-packed chromatography medium (sometimes referred to as the "stationary phase"). When liquid (sometimes referred to as the "liquid phase") is passed through the chromatography cartridge, at least a portion of the liquid phase adsorbs to the stationary phase within the cartridge. In this way, those components of the liquid phase that adsorb to the stationary phase are separated out from those that do not. Based on the different adsorption rates of various components of the liquid phase, the various components of the liquid phase can be isolated and identified.

When the cartridge is used, "channeling" can result if the medium is not tightly packed. If the medium is not tightly packed, the liquid phase in the chromatography system may find an "easy" path through the medium. That is, the liquid phase may not evenly progress through the stationary phase, but instead flow through discrete "channels" in the medium. If an easy flow path is available to the liquid because the medium is not tightly packed, the liquid may not interact as desired with the rest of the medium. The liquid phase will only interact with the medium along the "channels" through which it flows. Therefore, much of the medium will not be used, which may affect the performance of the chromatography cartridge and the accuracy of the chromatography results.

SUMMARY OF THE INVENTION

The method used to manufacture a chromatography cartridge can reduce channeling. For example, channeling can be controlled by the method used to couple an endcap to a housing portion of the cartridge. The method of coupling the endcap can affect, among other things, whether a hermetic (leak-proof) seal is established in the cartridge, whether the chromatography medium is tightly packed within the cartridge, whether the chromatography medium is maximally used in separation of various components of the liquid phase, and whether the chromatography system will produce repeatable, accurate results.

In one embodiment, the present invention comprises a chromatography cartridge. The chromatography cartridge includes a tubular housing having an open end and an inner surface, and a plug. The plug is positioned within the open end of the tubular housing and has an outer circumferential surface. A substantial portion of the outer circumferential surface is fused to the inner surface of the tubular housing.

In another embodiment, the present invention includes a method of manufacturing a chromatography cartridge, the chromatography cartridge comprising a housing having an open end and a longitudinal axis, and a plug dimensioned to be received in the open end of the housing. The method includes coupling at least a portion of the outer surface of the plug to at least a portion of the inner surface of the tubular housing in response to rotating at least one of the plug and the tubular housing about the longitudinal axis with respect to the other of the plug and the tubular housing.

In another embodiment, the present invention includes a chromatography cartridge comprising a tubular housing having a first wall thickness, and including a first portion formed of a first material, and a second portion formed of a second material, the second portion defining at least a portion of an outer surface of the tubular housing and having a second wall thickness less than the first wall thickness.

In another embodiment, the present invention includes a chromatography cartridge comprising a tube defining a longitudinal axis and including a relatively translucent first portion, and a relatively-opaque second portion, the relatively opaque second portion positioned substantially parallel to the longitudinal axis and being visible from the exterior of the tube.

In another embodiment, the present invention includes a chromatography cartridge comprising a tubular housing defining a longitudinal axis and including a relatively non-laser-writable first portion, and a relatively laser-writable second portion, the relatively laser-writable second portion being positioned substantially parallel to the longitudinal axis and defining at least a portion of an outer surface of the tubular housing to allow data to be printed on the outer surface of the housing with a laser.

In another embodiment, the present invention includes a method of manufacturing a chromatography cartridge, the method comprising: co-extruding a first material and a second material to form a housing comprising a first portion and a second portion, respectively, such that the second portion defines at least a portion of an outer surface of the housing, the second material including a laser mark additive; and printing data with a laser on the portion of the outer surface defined by the second portion.

In another embodiment, the present invention includes a disposable chromatography cartridge comprising: a tubular housing having a longitudinal center, the tubular housing including an end portion and a middle portion that includes the longitudinal center of the tubular housing; and at least one disposable retainer positioned circumferentially around the middle portion of the tubular housing to inhibit radial expansion of the tubular housing during chromatography.

Other features and aspects of the invention will become apparent to those skilled in the art upon review of the following detailed description, claims and drawings.

BRIEF DESCRIPTION OF THE DRAWINGS

FIG. 2 illustrates an assembled cross-sectional view of the chromatography cartridge of FIG. 1.

FIG. 3 illustrates another embodiment of a plug of a chromatography cartridge of the present invention.

FIG. 4 illustrates another embodiment of a plug of a chromatography cartridge of the present invention.

FIG. 8 illustrates a retainer according to one embodiment of the present invention.

FIG. 9 illustrates an assembled perspective view of the chromatography cartridge of FIGS. 6 and 7 with two of the retainer of FIG. 8.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings.

DETAILED DESCRIPTION

Figure 1:
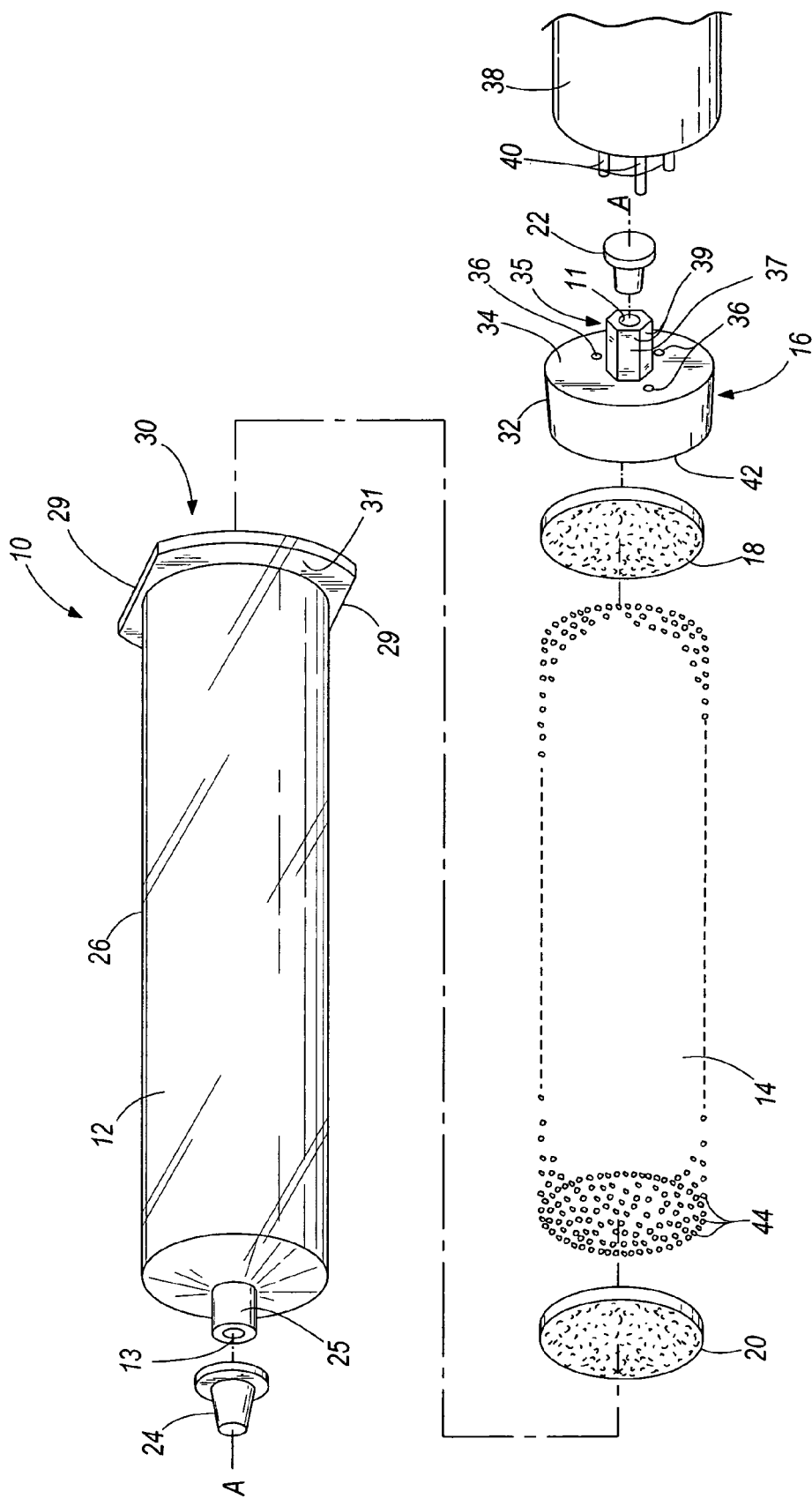
FIG. 1 illustrates an exploded perspective view of a chromatography cartridge having a housing and a plug, according to one embodiment of the present invention.

FIGS. 1 and 2 illustrate a chromatography cartridge 10 (also referred to herein as a chromatography "column") according to one embodiment of the present invention. The cartridge 10 contains at least one chromatography medium 14 (also referred to herein as a "stationary phase"), and an inlet 11 and an outlet 13 for fluid flow through the cartridge 10 and thereby the medium 14. The medium 14 is bounded on a first end by a first frit 18 or other porous member positioned towards the inlet 11, and on the second end by a second frit 20 positioned towards the outlet 13. The medium 14 is contained within a housing 12 that is capped on one end by a plug 16 (also referred to herein as and "endcap"). The plug 16 defines the inlet 11 to the cartridge 10. A first cap 22 is dimensioned to be received within the inlet 11 during transportation and storage, and a second cap 24 is dimensioned to cover the outlet 13 during transportation and storage.

The chromatography cartridge 10 can be used with a variety of chromatography systems including, without limitation, a flash chromatography system, and a variety of other liquid chromatography systems. The cartridge 10 can be formed of a variety of materials including without limitation, at least one of a metal, a polymer, a ceramic, a composite, and a combination thereof. As a result, in some embodiments of the present invention, the cartridge 10 can be a long-lasting cartridge that can be used for many chromatography processes. In other embodiments, the cartridge 10 can be formed of disposable materials such that a new chromatography cartridge 10 can be used for each new chromatography run.

In some embodiments, such as the embodiment illustrated in FIG. 1, the housing 12 can have an elongated, tubular shape and a generally uniform and annular cross-section. The housing 12 includes an outer surface 26, an inner surface 28, an open end 30, an annular flange 31 adjacent the open end 30. A longitudinal axis A-A runs the length of the cartridge 10. The outer surface 26, the inner surface 28 and the open end 30 all have a generally circular shape, as defined by the uniform and annular cross-sectional shape of the housing 12. It should be noted that the cross-sectional shape of the housing 12 can be a variety of other shapes or combinations of shapes without departing from the spirit and scope of the present invention including, without limitation, rectangular, square, triangular, hexagonal, and the like.

With continued reference to FIGS. 1 and 2, the annular flange 31 includes two flat sides 29. However, the annular flange 31 can instead continue around the generally circular open end 30 to form a completely annular flange 31 (i.e., without the flat sides 29). The annular flange 31 can be used to couple the housing 12 to a mechanical drive device during manufacturing of the cartridge 10, as will be described below, to couple the housing 12 to a variety of packing and storage materials for transportation and storage, and/or to couple the housing 12 to other equipment in a chromatography system during use.

As illustrated in FIGS. 1 and 2, the outlet 13 of the cartridge 10 can be defined in the housing 12. A bottom portion of the housing 12 tapers to form an exit tube 25 that defines the outlet 13. As fluid containing at least one sample of interest is injected into a chromatography system, the fluid is moved through the system to the inlet 11 of the cartridge 10, through a central bore 33 of the plug 16 (further described below), through the first frit 18, through the chromatography medium 14 where a variety of components of the fluid may interact with the chromatography medium 14, through the second frit 20, and out the outlet 13 defined in the exit tube 25.

The housing 12 and the plug 16 can be formed of a variety of materials including glass, stainless steel, ceramic, polyethylene, polypropylene, polyethylene terephthalate (PET), polyamide, polyvinyl chloride, polytetrafluoroethylene (e.g., TEFLON®-brand polytetrafluoroethylene (PTFE), DuPont Corporation), a polymer of tetrafluoroethylene and hexafluoropropylene (FEP; e.g., DYNEON™-brand FEP fluorothermoplastic, 3M Corporation), a fiberglass and PTFE composite (e.g., TEFLEX®-brand fiberglass sheets coated with TEFLON®-brand PTFE, DuPont Corporation), other chemically-inert materials, and the like. The housing 12 and the plug 16 can be formed of the same or different materials.

The plug 16 is dimensioned to be received within the open end 30 of the housing 12. The plug 16 has a generally cylindrical shape and includes an outer circumferential surface 32. The plug 16 further includes a tube 35 extending outwardly from an upper surface 34 of the plug 16, and the tube 35 defines the inlet 11. The plug 16 has an axially-extending central bore 33 such that the plug 16 has a generally annular cross-section, and the inlet 11 provides an opening to the central bore 33.

As illustrated in FIGS. 1 and 2, the tube 35 has a hexagonally-shaped outer surface 37 formed by six sides 39. The hexagonally-shaped outer surface 37 of the tube 35 can provide coupling surfaces for coupling the plug 16 to a mechanical drive device 38 during manufacturing of the cartridge 10, for coupling the plug 16 to packing or storage materials during transportation and storage of the cartridge 10, and/or for coupling the plug 16 to other equipment within a chromatography system during use. In other embodiments, the outer surface 37 can be cylindrical or can include a variety of numbers of sides 39 ranging from three sides 39 to as many as structurally possible. The shape of the outer surface 37 is at least partially dependent upon the chromatography system with which the cartridge 10 is used.

The tube 35 can be integrally formed with the remainder of the plug 16, as shown in FIG. 2, or the tube 35 can be coupled to the upper surface 34 by a variety of fasteners and/or adhesives known to those of ordinary skill in the art.

In some embodiments, the upper surface 34 of the plug 16 can include one or more axially-extending blind bores 36 defined therein and positioned to cooperate with a fixture of a mechanical drive device 38, as described in greater detail below. For example, as illustrated in FIGS. 1-3, the upper surface 34 of the plug 16 includes three axially-extending blind bores 36 positioned around the tube 35. Specifically, the blind bores 36 illustrated in FIG. 1 are arranged such that a blind bore 36 is positioned adjacent every other side 39 of the hexagonally-shaped outer surface 37.

The mechanical drive device 38, as illustrated in FIG. 1, can include three pins 40, each pin 40 dimensioned to be received within an axially-extending blind bore 36, such that upon rotation of the mechanical drive device 38, the cooperation of the pins 40 and the blind bores 36 causes rotation of the plug 16.

In other embodiments, such as the embodiment illustrated in FIG. 4, a plug 216 has an upper surface 234 that includes one or more radially-extending ribs 215 that cooperate with a fixture of a mechanical drive device. The radially-extending ribs 215 can extend outwardly from the upper surface 234 (as shown), can be formed inwardly as grooves (see, for example, FIGS. 6 and 9) into the upper surface 234, or can both extend outwardly and be formed inwardly. By way of example only, the upper surface 234 of the plug 216 illustrated in FIG. 4 includes three radially-extending ribs 215 that extend outwardly from the upper surface 234. The three radially-extending ribs 215 shown in FIG. 4 are positioned approximately 120 degrees apart from one another about the circular upper surface 234. The three radially-extending ribs 215 each extend radially across the upper surface 234 from a tube 235 that defines an inlet 211 to an edge 221 of the plug 16. In other embodiments, the radially-extending ribs 215 do not necessarily extend all the way to the edge 221, but rather extend radially across a portion of the upper surface 234. In still other embodiments, the radially-extending ribs 215 each have different lengths and extend varying radial distances across the upper surface 234.

A variety of mechanical drive devices can cooperate with the radially-extending ribs 215. For example, the pins 40 of the mechanical drive device 38 shown in FIG. 1 can be moved toward the upper surface 234 of the plug 216 until each pin 40 is either contacting the upper surface 234 or positioned a distance from the upper surface 234 less than the height of each radially-extending rib 215. (Alternatively, if the radially-extending ribs 215 are formed inwardly in the upper surface 234 (i.e., grooves), the pin 40 of the mechanical drive device 38 can be moved until each pin 40 has passed the upper surface 234 or is touching the base of each inwardly-formed rib 215.) Once each pin 40 is positioned near or in contact with the upper surface 234, the mechanical drive device 38 can be rotated. Upon rotation of the mechanical drive device 38, each pin 40 catches on each radially-extending rib 215, and causes the plug 216 to rotate.

As best illustrated in FIG. 2, the chromatography medium 14 is densely packed in the axial space between the first frit 18 and the second frit 20. The cartridge 10 can be manufactured by placing the second frit 20 adjacent the outlet 13 in a bottom portion of the housing 12, filling the housing 12 above the second frit 20 with at least one chromatography medium 14, placing the first frit 18 axially above the chromatography medium 14, and inserting the plug 16 into the open end 30 of the housing 12 to maintain the chromatography medium 14 axially between the first frit 18 and the second frit 20.

The plug 16 is inserted into the open end 30 of the housing 12 until at least a portion of a bottom surface 42 of the plug 16 contacts the first frit 18. By contacting the first frit 18 with at least a portion of the bottom surface 42 of the plug 16, the first frit 18 is maintained in a position that allows the chromatography medium 14 to remain densely packed between the first frit 18 and the second frit 20. Maintaining the first frit 18 at this position can enhance the performance of the chromatography cartridge 20 and can substantially prevent a liquid phase from channeling through the chromatography medium 14 in the cartridge 10.

Referring to FIGS. 1 and 2, the chromatography medium 14 is formed of particles 44. The particles 44 may vary in diameter. For example, particularly in flash chromatography, the diameter of the particles 44 may be specified as 50 $\mu$m, but actual particle diameters can range from approximately 32 $\mu$m to approximately 63 $\mu$m. The volume-to-mass ratio of the particles 44 in a cartridge 10 is referred to herein as the bulk density of the chromatography medium 14. The cartridge 10 can be filled with at least one chromatography medium 14 by volume rather than weight. Some cartridges 10 may have more, but smaller, particles 44 and some may have fewer, but larger, particles 44. Mainly because of this difference, the volume of the chromatography medium 14 filling the housing 12 can vary.

At least a portion of the outer circumferential surface 32 of the plug 16 is fused with the inner surface 28 of the housing 12. Particularly, at least a portion of the inner surface 28, adjacent the open end 30 of the housing 12, is fused to the outer circumferential surface 32 of the plug 16. Fusing at least a portion of the outer circumferential surface 32 of the plug 16 with the inner surface 28 of the housing 12 can maintain the first frit 18 in a desired axial position, can ensure that the at least one chromatography medium 14 remains densely packed throughout a chromatography process, and/or can provide a hermetic seal between the outer circumferential surface 32 of the plug 16 and the inner surface 28 of the housing 12.

In the embodiment illustrated in FIGS. 1 and 2, the outer circumferential surface 32 of the plug 16 has been spin-welded to the inner surface 28 of the housing 12. To spin-weld the outer circumferential surface 32 of the plug 16 to the inner surface 28 of the housing 12, at least one of the plug 16 and the housing 12 is coupled to a mechanical drive device, such as the mechanical drive device 38 shown in FIG. 1. For example, the plug 16 can be coupled to the mechanical drive device 38 as explained above, and/or the housing 12 can be coupled to a mechanical drive device by clamping a fixture about the outer surface 26 of the housing 12 and in abutting relation with the annular flange 31.

When the plug 16 and/or the housing 12 are coupled to a mechanical drive device, the mechanical drive device rotates the plug 16 and/or the housing 12 relative to the other of the plug 16 and the housing 12 about the longitudinal axis A-A. The plug 16 and/or the housing 12 are then axially moved relative to the other to engage the outer circumferential surface 32 of the plug 16 with the inner surface 28 of the housing 12 as the plug 16 and/or the housing 12 continue to be rotated. As the outer circumferential surface 32 of the plug 16 engages the inner surface 28 of the housing 12 while at least one of the plug 16 and the housing 12 are being rotated and moved relative to the other, the outer circumferential surface 32 of the plug 16 becomes spin-welded to the inner surface 28 of the housing 12. As will be readily understood by those of ordinary skill in the art, the spin-weld is created when the parts fuse together as a result of the heat generated by the friction between the rapidly spinning parts.

For example, the housing 12 can be held in a fixed position, and the mechanical drive device 38 is coupled to the plug 16 via the cooperation of the pins 40 with the axially-extending blind bores 36 (or the radially-extending ribs 215 illustrated in FIG. 4). The mechanical drive device 38 rotates the plug 16 relative to the housing 12 and moves the plug 16 into the open end 30 of the housing 12. The plug 16 is rotated about the longitudinal axis A-A and inserted into the open end 30 of the housing 12 simultaneously to create an annular interface, or annular frictional weld, between the outer circumferential surface 32 of the plug 16 and the inner surface 28 of the housing 12.

In some embodiments of the present invention, the plug 16 and/or the housing 12 can be rotated in one direction (i.e., clockwise or counter-clockwise). In other embodiments, the plug 16 and/or the housing 12 can be oscillated by rotating the plug 16 and/or the housing 12 a first amount in a first direction (e.g., clockwise) and then rotating the plug 16 and/or the housing 12 a second amount in a second direction opposite the first direction (e.g., counter-clockwise). The first amount does not need to be equal to the second amount, and in fact, the first amount can gradually increase and the second amount can gradually increase.

In some embodiments of the present invention, the plug 16 is inserted into the open end 30 of the housing 12 prior to rotation of the plug 16 and/or the housing 12. In other embodiments, the plug 16 is inserted at least partially into the open end 30 of the housing 12 prior to rotation of the plug 16 and/or the housing 12, and the plug 16 and/or the housing 12 are then axially moved relative to the other of the plug 16 and the housing 12 as the plug 16 and/or the housing 12 continue to be rotated.

The rotation of the plug 16 and/or the housing 12 continues until a predetermined interface temperature of the interface between the outer circumferential surface 32 and the inner surface 28 has been achieved, a predetermined number of rotations has been achieved, a predetermined number of oscillations has been achieved, a user or a control system aborts the process, and a combination thereof.

The movement of the plug 16 into the open end 30 of the housing 12 and/or the movement of the housing 12 over the plug 16 continues until at least one of the plug 16 and the housing 12 has been moved a predetermined distance, a predetermined insertion force from moving the plug 16 into the open end 30 of the housing 12 has been achieved, a predetermined insertion force from moving the open end 30 of the housing 12 over at least a portion of the plug 16 has been achieved, a first interface temperature between the outer circumferential surface 32 and the inner surface 28 has been achieved, at least a portion of the bottom surface 42 of the plug 16 has contacted the first frit 18 within the housing 12, at least a portion of the bottom surface 42 of the plug 16 has contacted the at least one chromatography medium 14 within the housing 12, a user or a control system aborts the operation, and a combination thereof.

FIG. 3 illustrates a cartridge 100 according to another embodiment of the present invention, wherein like numerals represent like elements to the embodiments described above. The cartridge 100 includes a housing 112 adapted to receive at least one chromatography medium 114, at least one frit 118 or other porous member (only one shown in FIG. 3 for simplicity), and a plug 116. The housing 112 includes an outer surface 126, an inner surface 128, an open end 130 and a longitudinal axis B-B.

The plug 116 includes an inner portion 117 dimensioned to be received within the open end 130 of the housing 112. The inner portion 117 of the plug 116 includes an outer circumferential surface 132, at least a portion of which is fused with at least a portion of the inner surface 128 of the housing 112 following the spin-welding method described above. The plug 116 includes an outer annular portion 119 integrally formed with the inner portion 117 of the plug 116. The outer annular portion 119 extends along the outer surface 126 of the housing 112 adjacent the open end 130. The outer annular portion 119 forms an aesthetic shroud or canopy to at least partially conceal from view the inner portion 117 of the plug 116. The aesthetic shroud formed by the outer annular portion 119 can also conceal at least a portion of the fused interface between the outer circumferential surface 132 of the plug 116 and the inner surface 128 of the housing 112 to form a more aesthetically-pleasing cartridge 100.

Figure 5:
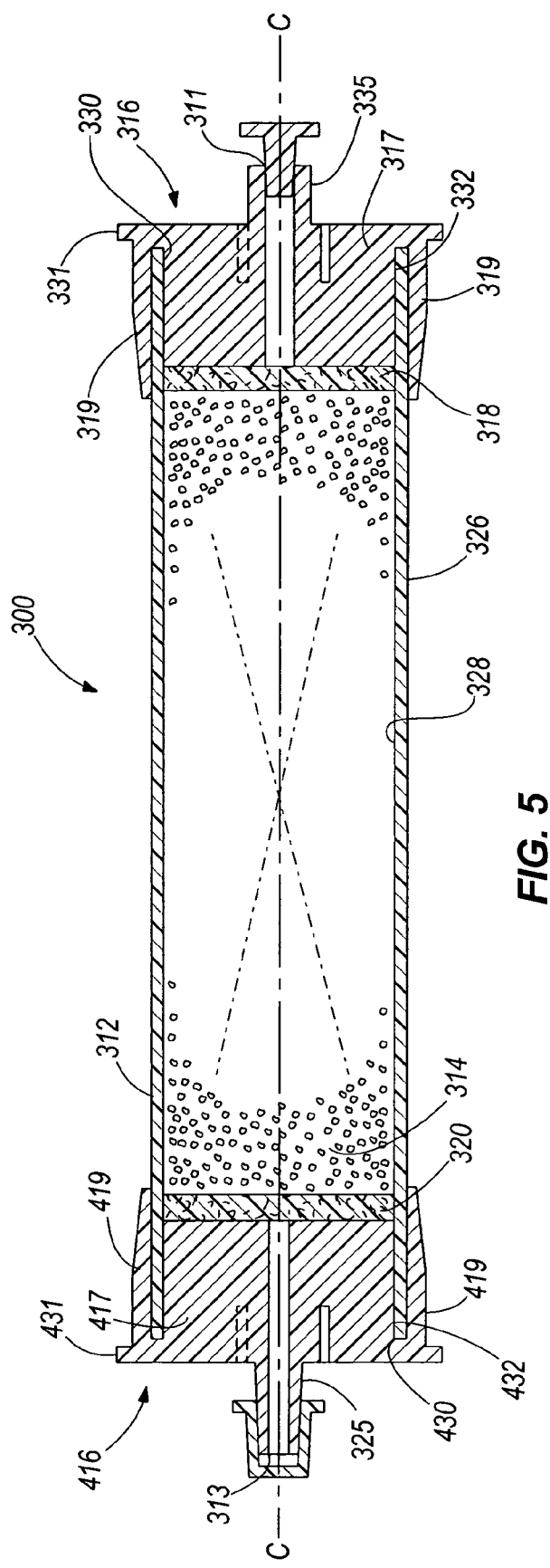
FIG. 5 illustrates another embodiment of a chromatography cartridge of the present invention.

FIG. 5 illustrates a chromatography cartridge 300 according to another embodiment of the present invention, wherein like numerals represent like elements to the embodiments described above. The cartridge 300 includes a housing 312 adapted to receive at least one chromatography medium 314, a first frit 318, a second frit 320, a first plug 316, and a second plug 416. The housing 312 includes an outer surface 326, an inner surface 328, a first open end 330, a second open end 430, and a longitudinal axis C-C. The first plug 316 and the second plug 416, similar to the plug 116 shown in FIG. 3 and described above, each include an inner portion 317 and 417, respectively, and an outer annular portion 319 and 419, respectively. The inner portions 317 and 417 of the first plug 316 and the second plug 416 each include an outer circumferential surface 332 and 432, respectively, at least a portion of which can be fused with at least a portion of the inner surface 328 of the housing 312, as described above with respect to the plug 116. The cartridge 300 can have any length desired, at least partially due to forming the housing 312 to any desired length. The first plug 316 and the second plug 416 can be fused to the housing 312 of the desired length to tightly compress the at least one chromatography medium 314 within the housing 312 to form the cartridge 300 to the desired length.

In the embodiment illustrated in FIG. 5, an inlet 311 of the cartridge 300 is defined in a tube 335 of the first plug 316, and an outlet 313 of the cartridge 300 is defined in a tube 325 of the second plug 416. The tubes 325 and 335 are similar to the tubes 25 and 35 shown in FIGS. 1 and 2. However, it should be noted that in other embodiments, the first plug 316 can be identical to the second plug 416, such that the tubes defining the inlet 311 and the outlet 313 are also identical.

The first plug 316 and the second plug 416 also each include a flange 331 and 431, respectively. The flanges 331 and 431 can be used to couple at least one of the first plug 316 and the second plug 416, respectively, to a mechanical drive device during manufacturing of the cartridge 300; to couple at least one of the cartridge 300, the first plug 316 and the second plug 416 to a variety of packing and storage materials for transportation and storage; and/or to couple the cartridge 300 to other equipment in a chromatography system during use.

Figure 6:
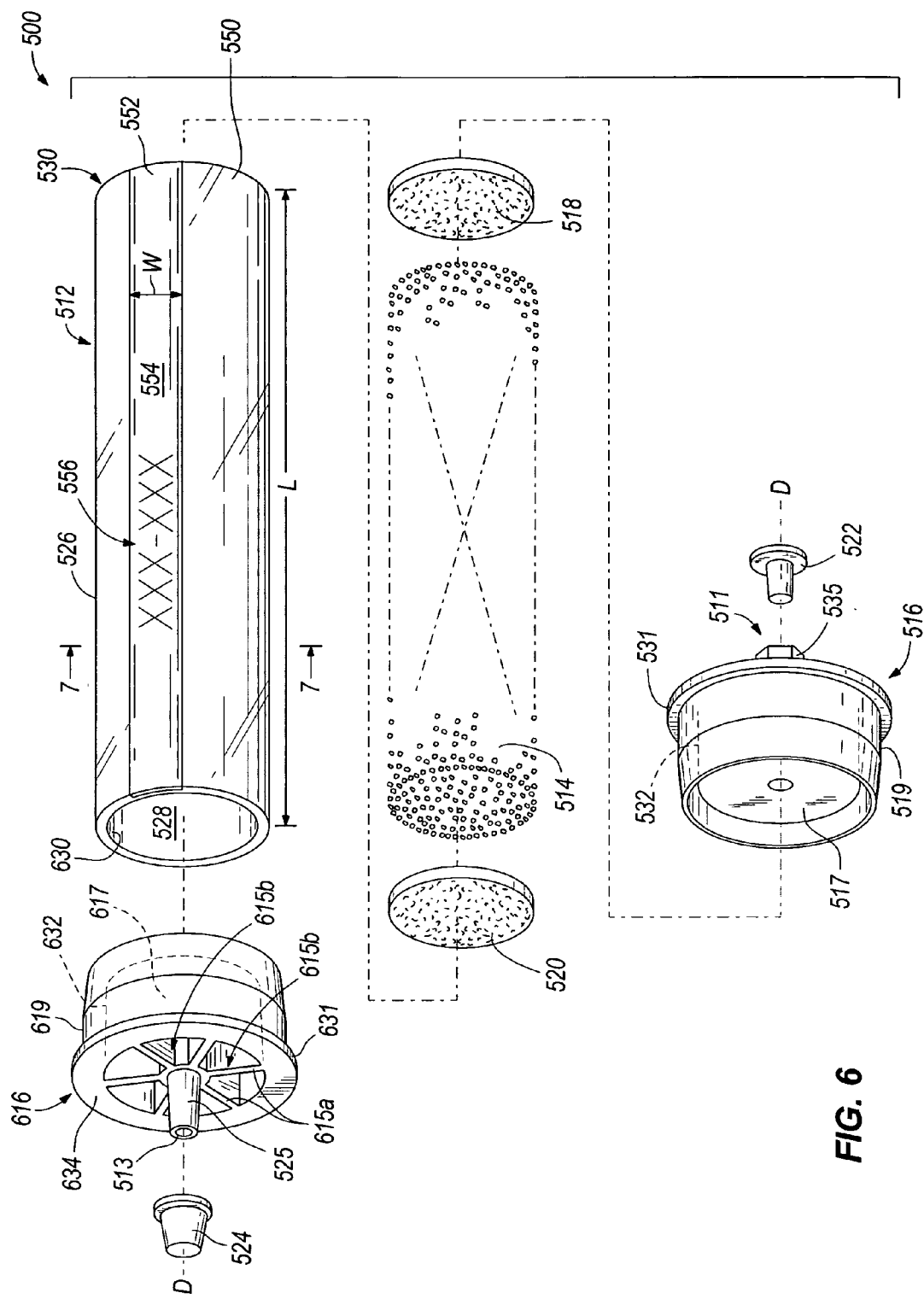
FIG. 6 illustrates an exploded perspective view of another embodiment of a chromatography cartridge of the present invention.
Figure 7:
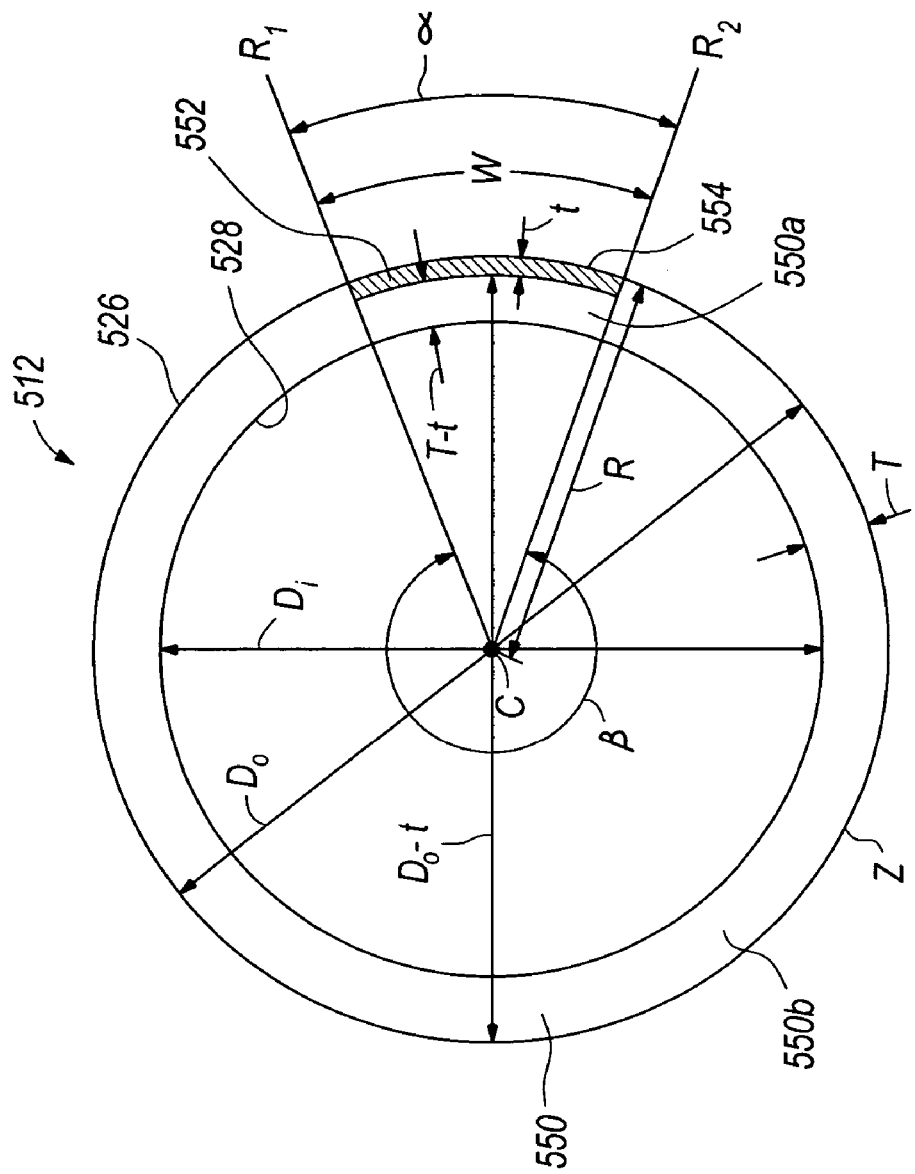
FIG. 7 illustrates a cross-sectional view of the chromatography cartridge of FIG. 6, taken along line 7-7.

FIGS. 6 and 7 illustrate a chromatography cartridge 500 according to another embodiment of the present invention, wherein like numerals represent like elements to the embodiments described above. The cartridge 500 shares many of the same elements and features described above with reference to the illustrated embodiment of FIG. 5. Reference is made to the description above accompanying FIG. 5 for a more complete description of the features and elements (and alternatives to such features and elements) of the embodiment illustrated in FIGS. 6 and 7.

The cartridge 500 includes a housing 512 adapted to receive at least one chromatography medium 514, a first frit 518, a second frit 520, a first plug 516, and a second plug 616. The housing 512 includes an outer surface 526, an inner surface 528, a first open end 530, a second open end 630, and a longitudinal axis D-D. The first plug 516 and the second plug 616 each include an inner portion 517 and 617, respectively, and an outer annular portion 519 and 619, respectively. The inner portions 517 and 617 of the first plug 516 and the second plug 616 each include an outer circumferential surface 532 and 632, respectively, at least a portion of which can be fused with at least a portion of the inner surface 528 of the housing 512. The cartridge 500 can have any length desired, at least partially due to forming the housing 512 to any desired length. The first plug 516 and the second plug 616 can be fused to the housing 512 of the desired length to tightly compress the at least one chromatography medium 514 within the housing 512 to form the cartridge 500 to the desired length. In some embodiments, the housing 512 is formed by extrusion, and the first and second plugs 516, 616 are formed by molding (e.g., injection molding).

As shown in FIG. 6, the first plug 516 includes a tube 535 that defines an inlet 511 of the cartridge 500, and the second plug 616 includes a tube 525 that defines an outlet 513 of the cartridge 500. A first cap 522 is dimensioned to be received within the inlet 511, and a second cap 524 is dimensioned to cover the outlet 513. The first plug 516 and the second plug 616 also each include a flange 531 and 631, respectively.

In some embodiments, as shown in FIG. 6, the second plug 616 includes a plurality of radially-extending ribs 615a and grooves 615b defined in an upper surface 634 of the second plug 616. The radially-extending grooves 615b extend along a substantial portion of the depth of the inner portion 617. The plurality of radially-extending ribs 615a and grooves 615b can be positioned and arranged to cooperate with a fixture of a mechanical drive device to fuse the second plug 616 to the housing 512. The first plug 516 of the embodiment illustrated in FIG. 6 includes similar structures, but such structures are not shown.

In the embodiment shown in FIG. 6, the housing 512 has a generally cylindrical tubular shape. As shown in FIGS. 6, the housing 512 has a length L. As shown in FIG. 7, the housing 512 has an outer circumference Z, an inner diameter $D_i$, an outer diameter $D_o$, and a wall thickness T. In some embodiments, the housing 512 is formed by extrusion to achieve a desired length L, outer circumference Z, inner diameter $D_i$, outer diameter $D_o$, and/or wall thickness T. In some embodiments, the housing 512 has an inner diameter $D_i$ of at least about 10 mm. In some embodiments, the housing 512 has an inner diameter $D_i$ of no greater than about 150 mm. In some embodiments, the housing 512 is extruded to a size that will permit a particular mass of chromatography medium 514 to be packed into the chromatography cartridge 500. In some embodiments, the mass of chromatography medium 514 used is at least about 4 g. In some embodiments, the mass of chromatography medium 514 used is no greater than about 350 g.

The housing 512, the first plug 516 and the second plug 616 can be formed of a variety of materials, including, but not limited to, polymers, particularly, homopolymers, and more particularly, clarified homopolymers (i.e., to produce a relatively translucent part, or a part that is approaching transparency).

In some embodiments of the present invention, the housing 512, the first plug 516 and the second plug 616 are all formed of the same, or very similar, material. In some embodiments, the respective portions of the housing 512 and the first and second plugs 516, 616 that are to be fused together are formed of the same, or very similar, material. In some embodiments, the same, or very similar, material is defined as a polymer having approximately the same melt flow index (MFI). For example, in some embodiments, at least the respective portions of the housing 512 and the first and second plugs 516, 616 are formed of a polymer having a MFI of at least about 3. In some embodiments, at least the respective portions of the housing 512 and the first and second plugs 516, 616 are formed of a polymer having a MFI of no greater than about 4.

In some embodiments of the present invention, one or more of the housing 512, the first plug 516 and the second plug 616 is colored (e.g., by a color additive). For example, in some embodiments, the housing 512 has a first color, and the first plug 516 and the second plug 616 have a second color. The color of one or more of the housing 512, the first plug 516 and the second plug 616 can be used for visual identification of the cartridge 500. For example, the color of the first and second plugs 516, 616 can be used to indicate, without limitation, one or more of the following: size characteristics of the cartridge 500 (e.g., the mass, length L, outer circumference Z, inner diameter $D_i$, outer diameter $D_o$, and/or wall thickness T of the housing 512), the type of chromatography medium 514 used in the cartridge 500, the quantity of chromatography medium 514 used in the cartridge 500, etc.

In some embodiments of the present invention, as shown in FIGS. 6 and 7, the housing 512 is formed of a first portion 550 and a second portion 552. The first portion 550 is formed of a first material, and the second portion 552 is formed of a second material. In embodiments in which the housing 512 is extruded, the first portion 550 and the second portion 552 can be formed by co-extrusion.

In some embodiments, the first material and the second material comprise the same, or very similar, material. For example, the first and second materials can each include a clarified homopolymer, such as those described above. In some embodiments, the second material further includes a colorant, as known to those of ordinary skill in the art, to produce a colored material. The color of the second material can include at least one of red, blue, yellow, orange, green, purple, gray, black, and combinations thereof.

The second material can further include a laser mark additive, and accordingly, the second portion 552 can define a laser-writable surface 554. The laser mark additive allows the second material to absorb the wavelength of a laser. An example of a laser mark additive that can be used with the present invention is Lazerflair® laser mark additive, available from EMD Chemicals, Inc. In some embodiments, the colorant for the second material includes a laser mark additive. For example, a colorant available from Clariant Masterbatches includes a colorant and Lazerflair® laser mark additive (EMD Chemicals, Inc.).

The color of the second material and the laser mark additive used can be selected based on the type of laser used to write data 556 onto the laser-writable surface 554. The laser can include at least one of a Nd:YAG laser, a frequency-doubled Nd:YAG laser, a frequency-tripled Nd:YAG laser, a carbon dioxide laser, a holmium laser, and combinations thereof. In some embodiments, the laser has a wavelength of less than or equal to approximately 1064 nm. The laser can chemically transform a portion of the second material in order to write the data 556 onto the laser-writable surface 554. The portion of the second material that is transformed by the laser can be transformed to a color including at least one of gray, black, and combinations thereof. Accordingly, the color of the second material can be chosen to allow improved visualization of the portion transformed by the laser.

A variety of data 556 can be written with a laser onto the laser-writable surface 554. For example, the data 556 can include one or more of the following: a company name, a company logo, a product name, a product logo, a serial number, a lot number, size characteristics for the chromatography cartridge, type of chromatography medium used in the chromatography cartridge, quantity of chromatography medium used in the chromatography cartridge, a machine readable code (e.g., a barcode, a 2D PDF symbol, etc.) to encode any of the above information, and combinations thereof.

The first portion 550 has a length equal to the length L of the housing 512, defines a portion of the outer surface 526 of the housing 512, and defines the inner surface 528 of the housing 512.

The second portion 552 has a length equal to the length L of the housing 512. The second portion 552 defines at least a portion of the outer surface 526, and accordingly, at least a portion of the outer circumference Z of the housing 512. The distance the second portion 552 extends along the outer circumference Z of the housing 512 (i.e., the arc length) is referred to herein as the "width" W of the second portion 552. In some embodiments, the width W is at least about 0.125 inches. In some embodiments, the width W is no greater than about 0.75 inches. In some embodiments, the width W is equal to the outer circumference Z of the housing 512.

As shown in FIG. 7, the housing 512 has a center C and an outer radius R, which is equal to half of the outer diameter $D_o$. The second portion 552 is bound by a first imaginary radial line $R_1$ that extends from the center C and a second imaginary radial line $R_2$ that extends from the center C that is separated from the first imaginary radial line $R_1$ by a central angle $\alpha$. Thus, the width W of the second portion 552 is an arc length equal to $\pi \cdot R \cdot \alpha/180$. The angle $\alpha$ can have a variety of values up to 360 degrees. For example, in some embodiments, the angle $\alpha$ is at least about 30 degrees. In some embodiments, the angle $\alpha$ is no greater than about 60 degrees.

The second portion 552 has a uniform wall thickness t. In some embodiments, the wall thickness t of the second portion 552 is not uniform, but varies along the width W. In some embodiments, such as the embodiment illustrated in FIGS. 6 and 7, the wall thickness t of the second portion 552 is less than the wall thickness T of the housing 512. Accordingly, as shown in FIG. 7, the second portion 552 does not define the inner surface 528 of the housing 512. In embodiments in which the second material includes a laser mark additive, the second material may not be inert to the chromatography process (i.e., inert relative to the chromatography medium 514, the liquid phase, etc.). By allowing the wall thickness t of the second portion 552 to be less than the wall thickness T of the housing 512 in such embodiments, the second material can be prevented from directly interacting with the interior of the housing 512 and the chromatography process.

In embodiments in which the wall thickness t of the second portion 552 is less than the wall thickness T of the housing 512, the first portion 550 has a varying wall thickness. The first imaginary radial line $R_1$ and the second imaginary radial line $R_2$ are also separated by a central angle $\beta$, wherein $\beta=360$ degrees$-\alpha$. The first portion 550 has an alpha portion 550a, which subtends the angle $\alpha$, and a beta portion 550b, which subtends the angle $\beta$. The wall thickness of the beta portion 550b is equal to the wall thickness T of the housing 512. The wall thickness of the alpha portion 550a is equal to the difference between the wall thickness T of the housing 512 and the wall thickness t of the second portion 552 (i.e., T$-$t). Similarly, in such embodiments, the first portion 550 has a varying outer diameter. The outer diameter of the beta portion 550b is equal to the outer diameter $D_o$ of the housing 512, and the outer diameter of the alpha portion 550a is equal to the difference between the outer diameter $D_o$ of the housing 512 and the wall thickness t of the second portion 552 (i.e., $D_o-$t).

In the embodiment illustrated in FIGS. 6 and 7, the first portion 550 of the housing 512 is relatively translucent, and the second portion 552 is relatively opaque, depending on the wall thickness t, the color of the second portion 552, and the type of second material that is used (or the type of laser mark additive used).

In some embodiments, the housing 512 includes a plurality of second portions 552, and accordingly, a plurality of laser-writable surfaces 554. Each of the plurality of second portions 552 can have the same width W and the same wall thickness t, or the plurality of second portions 552 can have varying widths W and wall thicknesses t. The first portion 550, accordingly, forms the remaining portions of the housing 512. The plurality of second portions 552 can be formed of the same material (e.g., the same laser mark additive), or one or more of the plurality of second portions 552 can be formed of a different material.

FIG. 8 illustrates a retainer 700 according to one embodiment of the present invention. The retainer 700 can be positioned circumferentially around any of the chromatography cartridges 10, 100, 300 and 500 described herein. Specifically, the retainer 700 can be coupled to the outer surface 26, 126, 326, 526 of the cartridge 10, 100, 300, 500 to inhibit radial expansion of the housing 12, 112, 312, 512 during use of the cartridge 10, 100, 300, 500 in a chromatography process.

The retainer 700 includes a band 702 and a buckle 704 that allows the band 702 to be tightened and wrapped around a chromatography cartridge, such as one of the chromatography cartridges 10, 100, 300, 500 described above. Particularly, the band 702 can be fed through the buckle 704 to form a circular shape, the diameter of which can be decreased by tightening the buckle 704 on the band 702. The retainer 700 can be wrapped around a variety of cartridge shapes. However, in some embodiments, such as the embodiment illustrated in FIG. 8, the retainer 700 is especially useful with generally cylindrical cartridges, such as the cartridges 10, 100, 300, 500 described herein. Accordingly, the retainer 700 includes an inner circumferential surface 706 that defines an inner circumference 708.

The band 702 and the buckle 704 can be formed of separate elements that are coupled together, or the band 702 and the buckle 704 can be integrally formed. The band 702 includes a length Q, width X, and thickness S, all of which can be varied to accommodate a variety of cartridges. For example, in some embodiments, the band 702 can include a width X of at least about 0.50 inches. In some embodiments, the band 702 can include a width X of no greater than about 0.75 inches.

The retainer 700 can be formed of a variety of materials, including, without limitation, steel and stainless steel. For example, the BAND-IT Jr.™ product line, available from BAND-IT-IDEX, Inc., which is formed of galvanized carbon steel can be used for the retainer 700. The retainer 700 can be disposable, such that a disposable cartridge 10, 100, 300, 500 that includes the retainer 700 remains a disposable product without requiring removal of the retainer 700 prior to disposal.

The retainer 700 is illustrated and described above by way of example only. Other disposable retainers performing the same function can be used without departing from the spirit and scope of the present invention.

FIG. 9 shows the chromatography cartridge 500 in an assembled state, with two of the retainers 700 shown in FIG. 8. The chromatography cartridge 500 is illustrated in FIG. 9 by way of example only, but it should be understood that any of the cartridges 10, 100, 300 and 500 described herein can be used with the retainer 700. A first retainer 700a having a first band 702a and a first buckle 704a is shown in a partially assembled state, and the band 702a of the first retainer 700a includes a free end 710a. A second retainer 700b having a second band 702b and a second buckle 702b is shown in a fully assembled state.

The first band 702a of the first retainer 700a has been tightened in the first buckle 704a about the outer circumference Z of the housing 512. The inner circumferential surface (not visible in FIG. 9) of the first retainer 702a is substantially flush with the outer surface 526 of the housing 512, such that the inner circumference (not visible in FIG. 9) of the first retainer 700a is approximately equal to the outer circumference Z of the housing 512. The free end 710a of the first band 702a remains unsecured, and accordingly, the first retainer 700a is partially assembled.

The second band 702b has been tightened in the second buckle 704b about the outer circumference Z of the housing 512, similar to that of the first retainer 700a. The second band 702b has been bent at the second buckle 704b such that the second band 702b is wrapped over the second buckle 704b and a portion of itself. In addition, the second band 702b can be crimped in this position over the second buckle 704b to secure the second retainer 700b to the housing 512 in a fully assembled state.

In addition, the distance between the first retainer 700a and the second retainer 700b can be determined based on the data 556 printed on the laser-writable surface 554 of the cartridge 500. Alternatively, the data 556 printed on the laser-writable surface 554 can be printed in such a way that the data 556 is visible when the retainers 700 are in a fully assembled state.

The retainers 700 can be secured to the cartridge 500 at any point in the manufacturing process of the cartridge 500. That is, the retainers 700 need not be secured to the cartridge 500 at the end of the assembly or manufacturing process. For example, the retainers 700 can be secured to the housing 512 prior to coupling either of the first and second plugs 516, 616 to the housing 512, after coupling the first plug 516 to the housing but prior to coupling the second plug 616 to the housing 512, etc.

By way of example only, in some embodiments, the chromatography cartridge 500 as it is shown in FIG. 9 is manufactured in the following order (some steps in the manufacturing process not included for simplicity): (1) securing the first and second retainers 700a, 700b in their fully assembled stated about the housing 512, (2) fusing the first plug 516 to the housing 512, (3) inserting the first frit 518 into the housing 512 adjacent the first plug 516, (4) filling the housing 512 with the chromatography medium 514, (5) inserting the second frit 520 into the housing 512, and (6) fusing the second plug 616 to the housing 512. Any of the above six steps can be performed substantially simultaneously.

By way of further example, in other embodiments, the chromatography cartridge 500 as it is shown in FIG. 9 is manufactured in the following order (some steps in the manufacturing process not included for simplicity): (1) fusing the first plug 516 to the housing 512, (2) inserting the first frit 518 into the housing 512 adjacent the first plug 516, (3) filling the housing 512 with the chromatography medium 514, (4) inserting the second frit 520 into the housing 512, (5) fusing the second plug 616 to the housing 512, and (6) securing the first and second retainers 700a, 700b in their fully assembled stated about the housing 512. Any of the above six steps can be performed substantially simultaneously.

In some embodiments, only one retainer 700, or more than two retainers 700 can be positioned around the housing 12, 112, 312, 512 of the cartridge 10, 100, 300, 500. For example, in some embodiments of the present invention, only one retainer 700 is positioned around the housing 12, 112, 312, 512 of the cartridge 10, 100, 300, 500, and the single retainer 700 is positioned centrally with respect to the length L of the housing 12, 112, 312, 512 (i.e., at the longitudinal center of the housing 12, 112, 312, 512). In some embodiments, an even number of two or more retainers 700 are positioned around the housing 12, 112, 312, 512 of the cartridge 10, 100, 300, 500, and the retainers 700 are positioned such that each of a pair of two retainers 700 is equally spaced from the longitudinal center of the housing 12, 112, 312, 512. For example, in some embodiments, if there are two retainers 700, each one is spaced an equal distance along the length L of the housing 12, 112, 312, 512 from the longitudinal center of the housing 12, 112, 312, 512. In some embodiments, if there are four retainers 700, each of a first pair of retainers 700 is spaced an equal distance from the longitudinal center, and each of a second pair of retainers 700 is spaced an approximately equal distance from the longitudinal center). In some embodiments, an odd number of one or more retainers 700 is positioned around the housing 12, 112, 312, 512 of the cartridge 10, 100, 300, 500. The retainers 700 in such embodiments are positioned such that a first retainer 700 is positioned around the longitudinal center of the housing 12, 112, 312, 512, and any additional retainers 700 are spaced equally along the length L of the housing 12, 112, 312, 512 from the first retainer 700.

The number of retainers 700, and the distance between retainers 700 along the length of the housing 12, 112, 312, 512 can depend on the size of the cartridge 10, 100, 300, 500 used. For example, in some embodiments, a retainer 700 is positioned about every 4 inches along the length of the housing 12, 112, 312, 512. By way of further example, in embodiments in which the housing 12, 112, 312, 512 is about two feet long, four or five retainers 700 can be spaced apart along the length of the housing 12, 112, 312, 512. In some embodiments, the distance between adjacent retainers 700 is the same along the length of the housing 12, 112, 312, 512, and in some embodiments, the distance between adjacent retainers 700 varies.

Various features and aspects of the invention are set forth in the following claims.

The invention claimed is:

1. A chromatography cartridge comprising:
   a tubular housing having a first wall thickness, the tubular housing including a first open end, a second open end, and an inner volume defined between the first open end and the second open end;
   a first portion of the tubular housing formed of a first material, and
   a second portion of the tubular housing formed of a second material, the second portion defining a stripe on an outer surface of the tubular housing, the stripe extending substantially the length of the tubular housing and having a second wall thickness less than the first wall thickness;
   a plug including an annular groove adapted to receive one of the first open end and the second open end, a first portion of the plug positioned through the open end and into the inner volume and having an outer circumferential surface, a substantial portion of the outer circumferential surface having a length greater than the first wall thickness of the tubular housing and being fused to an inner surface of the tubular housing, and a second portion of the plug positioned outside the inner volume and extending toward the opposite open end, the second portion of the first plug extending along and overlapping a portion of an outer surface of the tubular housing, the plug including an aperture in fluid communication with the inner volume, and a protruding extension through which the aperture extends;
   a first frit positioned in the inner volume of the tubular housing, the first frit having a first surface oriented substantially parallel to a lateral surface of the first portion of the plug, the first surface of the first frit being in contact with the lateral surface of the first portion of the plug;

a second frit positioned in the inner volume of the tubular housing and adjacent the second open end; and a chromatography medium positioned between the first frit and the second frit.

2. The chromatography cartridge of claim 1, wherein the first portion is relatively translucent, and the second portion is relatively opaque.

3. The chromatography cartridge of claim 1, wherein the first portion is relatively non-laser-writable, and the second portion is relatively laser-writable to allow data to be laser-written on the outer surface of the tubular housing.

4. The chromatography cartridge of claim 1, wherein the first portion is formed of a clarified homopolymer.

5. The chromatography cartridge of claim 1, wherein the tubular housing has a first length, and the second portion has a second length substantially equal to the first length.

6. The chromatography cartridge of claim 1, wherein the second wall thickness is at least about 0.020 inches.

7. The chromatography cartridge of claim 1, wherein the second wall thickness is no greater than about 0.033 inches.

8. The chromatography cartridge of claim 1, wherein the second wall thickness is about 16% of the first wall thickness.

9. The chromatography cartridge of claim 1, wherein the tubular housing is formed by extrusion, and wherein the first portion and the second portion are co-extruded.

10. The chromatography cartridge of claim 1, wherein the tubular housing includes an inner surface, and wherein the plug positioned within one of the first open end and second open end includes an outer circumferential surface, a substantial portion of the outer circumferential surface being fused to the inner surface of the tubular housing.

11. The chromatography cartridge of claim 1, further comprising at least one retainer coupled to the outer surface of the tubular housing to inhibit radial expansion of the tubular housing during chromatography.

12. The chromatography cartridge of claim 1, wherein the tubular housing includes an annular cross-section, the annular cross-section having a center, the tubular housing further comprising:

a first imaginary radial line that extends from the center; and a second imaginary radial line that extends from the center, the second imaginary radial line being separated from the first imaginary radial line by an angle of about 30 degrees to about 60 degrees, the second portion of the tubular housing being bound by the first imaginary radial line and the second imaginary radial line.

13. The chromatography cartridge of claim 1, wherein the tubular housing has a circumference, and wherein the second portion has a width on the outer surface in the direction of the circumference of the tubular housing, and wherein the width is between about 0.125 inches and 0.750 inches.

14. A chromatography cartridge comprising:

a tube defining a longitudinal axis and including an inner volume, a first open end and a second open end, a relatively translucent first portion, and a relatively opaque second portion, the relatively opaque second portion positioned substantially parallel to the longitudinal axis and being visible from the exterior of the tube;

a plug including an annular groove adapted to receive one of the first open end and the second open end, a first portion of the plug positioned through the open end and into the inner volume and having an outer circumferential surface, a substantial portion of the outer circumferential surface having a length greater than the first wall thickness of the tubular housing and being fused to an inner surface of the tubular housing, and a second portion of the plug positioned outside the inner volume and extending toward the opposite open end, the second portion of the first plug extending along and overlapping a portion of an outer surface of the tubular housing, the plug including an aperture in fluid communication with the inner volume, and a protruding extension through which the aperture extends;

a first frit positioned in the inner volume of the tubular housing, the first frit having a first surface oriented substantially parallel to a lateral surface of the first portion of the plug, the first surface of the first frit being in contact with the lateral surface of the first portion of the plug;

a second frit positioned in the inner volume of the tubular housing and adjacent the second open end; and a chromatography medium positioned between the first frit and the second frit.

15. The chromatography cartridge of claim 14, wherein the second portion is relatively laser-writable and the first portion is relatively non-laser-writable.

16. The chromatography cartridge of claim 14, wherein the second portion includes data laser-written thereon.

17. The chromatography cartridge of claim 14, wherein the relatively opaque second portion is a different color than the relatively translucent first portion and includes at least one of red, blue, yellow, orange, green, purple, gray, black, and combinations thereof.

18. The chromatography cartridge of claim 14, wherein the relatively translucent first portion is formed of a clarified homopolymer.

19. The chromatography cartridge of claim 14, wherein the tube has a first wall thickness, and wherein the relatively opaque second portion has a second wall thickness that is less than the first wall thickness.

20. A chromatography cartridge comprising:

a tubular housing defining a longitudinal axis and including an inner volume, and an open end, a relatively non-laser-writable first portion, and a relatively laser-writable second portion, the relatively laser-writable second portion being positioned substantially parallel to the longitudinal axis and defining at least a portion of an outer surface of the tubular housing to allow data to be printed on the outer surface of the housing with a laser;

a plug including an annular groove adapted to receive the open end, a first portion of the plug positioned through the open end and into the inner volume and having an outer circumferential surface, a substantial portion of the outer circumferential surface having a length greater than a wall thickness of the tubular housing and being fused to an inner surface of the tubular housing, and a second portion of the plug positioned outside the inner volume and extending toward an opposite open end, the second portion of the first plug extending along and overlapping a portion of the outer surface of the tubular housing, the plug including an aperture in fluid communication with the inner volume, and a protruding extension through which the aperture extends;

a first frit positioned in the inner volume of the tubular housing, the first frit having a first surface oriented substantially parallel to a lateral surface of the first portion of the plug, the first surface of the first frit being in contact with the lateral surface of the first portion of the plug;

a second frit positioned in the inner volume of the tubular housing and adjacent the second open end; and a chromatography medium positioned between the first frit and the second frit.

21. The chromatography cartridge of claim 20, wherein the laser includes at least one of a Nd:YAG laser, a frequency-doubled Nd:YAG laser, a frequency-tripled Nd:YAG laser, a carbon dioxide laser, a holmium laser, and combinations thereof.

22. The chromatography cartridge of claim 20, wherein the relatively non-laser-writable first portion is relatively translucent, and the relatively laser-writable second portion is relatively opaque.

23. The chromatography cartridge of claim 20, wherein the relatively non-laser-writable first portion and the relatively laser-writable second portion are different colors, and the relatively laser-writable second portion includes at least one of red, blue, yellow, orange, green, purple, gray, black, and combinations thereof.

24. The chromatography cartridge of claim 20, wherein the relatively non-laser-writable first portion is formed of a clarified homopolymer.

25. The chromatography cartridge of claim 20, wherein the tubular housing has a first wall thickness, and wherein the relatively laser-writable second portion has a second wall thickness that is less than the first wall thickness.

26. The chromatography cartridge of claim 20, wherein the data includes at least one of a company name, a company logo, a product name, a product logo, a machine readable code, a serial number, a lot number, size characteristics for the chromatography cartridge, type of chromatography medium used in the chromatography cartridge, quantity of chromatography medium used in the chromatography cartridge, and combinations thereof.

* * * * *